(12) United States Patent
Morris

(10) Patent No.: US 6,992,731 B1
(45) Date of Patent: Jan. 31, 2006

(54) ELECTRO-OPTIC LENS HAVING MULTIPLE RESPONSIVE REGIONS OF A VARIABLE DEGREE OF LIGHT TRANSMISSION, METHOD OF FABRICATION THEREOF AND METHOD OF OPERATION THEREOF

(76) Inventor: Mitchell Joseph Aiosa Morris, 100 Old Lyme Rd., Purchase, NY (US) 10577

( * ) Notice: Subject to any disclaimer, the term of this patent is extended or adjusted under 35 U.S.C. 154(b) by 724 days.

(21) Appl. No.: 09/699,776

(22) Filed: Oct. 30, 2000

Related U.S. Application Data

(60) Provisional application No. 60/161,986, filed on Oct. 28, 1999, and provisional application No. 60/161,985, filed on Oct. 28, 1999.

(51) Int. Cl.
*G02F 1/1335* (2006.01)

(52) U.S. Cl. .......................................... 349/13; 349/14
(58) Field of Classification Search ............. 349/13–16; 351/45

See application file for complete search history.

(56) References Cited

U.S. PATENT DOCUMENTS

| 4,241,286 A | 12/1980 | Gordon |
| 5,113,270 A | 5/1992 | Fergason |
| 5,208,688 A | 5/1993 | Fergason et al. |
| 5,276,539 A | 1/1994 | Humphrey |
| 5,519,522 A | 5/1996 | Fergason |
| 5,751,258 A | 5/1998 | Fergason et al. |

*Primary Examiner*—Robert H. Kim
*Assistant Examiner*—T. L. Rude

(57) ABSTRACT

The present invention is directed to a lens having a variable light transmission in response to variations in incident light intensity. The lens is useful for providing eye protection from variations in ambient light intensity. The present invention is directed to shade devices having lenses which have a variable degree of light transmission which automatically changes in response to the intensity of incident light or at the selection of a user of the eye glasses.

2 Claims, 22 Drawing Sheets

ELECTRO-OPTIC LENS HAVING MULTIPLE RESPONSIVE REGIONS OF A VARIABLE DEGREE OF LIGHT TRANSMISSION, METHOD OF FABRICATION THEREOF AND METHOD OF OPERATION THEREOF

The priority of U.S. application Ser. No. 60/161,986, filed on Oct. 28, 1999 and entitled ELECTO-OPTIC LENS HAVING A VARIABLE DEGREE OF LIGHT TRANSMISSION AND METHOD OF OPERATION THEREOF is claimed; the teaching of which is incorporated herein by reference.

The priority of U.S. application Ser. No. 60/161,985, filed on Oct. 28, 1999 and entitled METHOD AND APPARATUS FOR DETERMINING AN EXTREMA PATH BETWEEN NODES OF AN ARRAY USING A DNA ALGORITHM, is claimed; the teaching or which is incorporated herein by reference.

FIELD OF THE INVENTION

The present invention is directed to a lens, methods of fabrication thereof and methods of use thereof, having a variable light transmission in response to variations in incident light intensity. The lens is useful for providing eye protection from variations in ambient light intensity. In particular, the present invention is directed to a pair of glasses having lenses that have a variable degree of light transmission in response to the intensity of incident light or at the selection of a user of the eye glasses.

BACKGROUND

Eye protection devices typically have a fixed optical transmission which reduced the intensity of light, incident on the eye protection device, that reaches the eyes of a user of the eye protection device. Thus there is a fixed attenuation of the incident light. For example, sun glasses typically have a fixed shade, i.e., a fixed transmission. Sun glasses are available which change transmitivity from a clear to a darker state in response to the intensity of the incident light based on a chemical response of constituents in the lens. Such sun glasses have the disadvantage that change from the clear to the dark state is fixed by the chemical process. That is, the user of the sun glasses cannot select the degree of transmission that the sun glasses have in response to a given incident intensity of light. The degree of transmission in response to a given intensity of light is set by the amount of the chemically active agent in the sun glasses that is fixed at manufacture and it, thus, cannot subsequently be changed by the user. Moreover, the chemical process of change from the clear to the dark state and visa versa is slow. Furthermore, the color of the dark state is fixed.

Applicant's invention provides a solution to this problem. According to applicants invention the degree of change in optical transmission from a clear to a dark state can be controlled by the user. Thus different users can select the degree of transmission that is suitable to them. Also, the same user may find it desirable to have a different degree of transmission in different environments. For example, for a given incident intensity of light a user may desire a greater degree of attenuation of the light intensity at a beach than while walking on a city street. Moreover, according to applicant's invention the change from the clear to the dark state and visa versa is rapid. Thus, for example, is driving an automobile on a sunny day and enters a tunnel the transmission can change rapidly from the dark to the clear state when entering the tunnel and rapidly from the clear to the dark state when exiting the tunnel. In addition, according to applicant's invention the color of the lens can be selected by the user from a large variety of colors. Thus a user can, depending on the circumstances, select a different color for a different occasion.

BRIEF DESCRIPTION OF THE DRAWINGS

The above and other objects and features of the invention will become more apparent from the following detailed description taken in connection with the accompanying drawings that form a part of this specification, and in which.

SUMMARY

Figure 1:
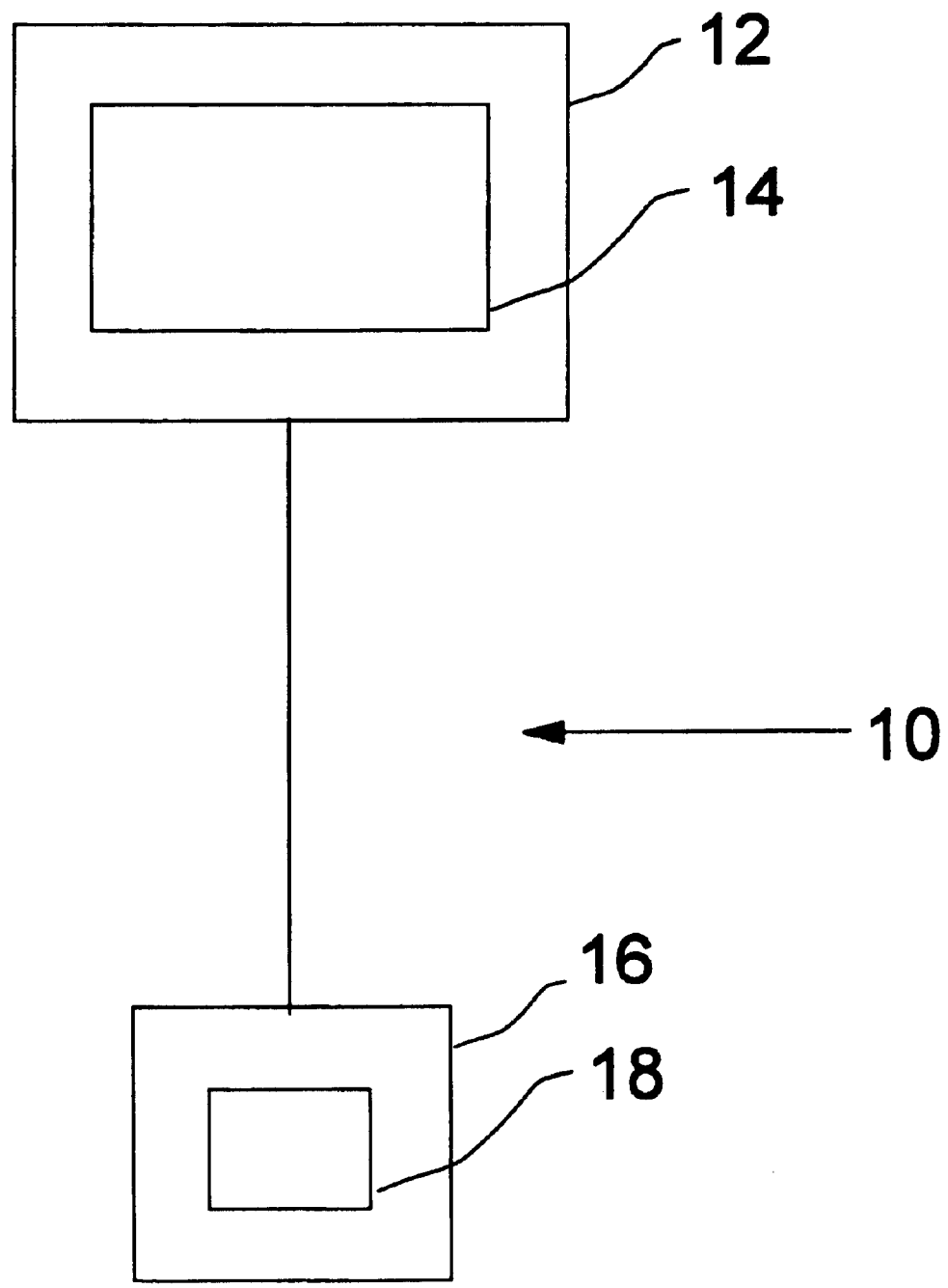
FIG. 1 is a schematic view of an eye protection device according to the present invention.

A broad aspect of the present invention is a lens (and methods of fabrication thereof and methods of use thereof) that has a variable light transmission in response to variations in incident light intensity.

Another broad aspect of the present invention is a lens (and methods of fabrication thereof and methods of use thereof) having a variable light transmission in response to user selection.

Another broad aspect of the present invention is a computer controlled shade (and methods of fabrication thereof and methods of use thereof) having a variable light transmission in response to a plurality of light sensitive regions.

In a more particular aspect of the present invention the lens having a variable transmitivity comprises an electo-optic lens and a variable power source (for example, a variable voltage source and a variable current source) for controlling the transmitivity of the electro-optic lens.

In another more particular aspect of the present invention the variable light transmission (transmitivity) comprises a variation in the intensity of the transmission, a variation in the color of the transmission and a combination thereof.

In another more particular aspect of the present invention the lens comprises an eye protection apparatus.

In another more particular aspect of the present invention the variable voltage source comprises a manual control to vary the power source.

In another more particular aspect of the present invention the variable power source comprises a photosensitive control to vary the power source in response to the intensity of light incident on the lens or eye protection apparatus.

In another more particular aspect of the present invention the lens or eye protection device can be switched between manual and automatic modes of operation.

In another more particular aspect of the present invention the electro-optic lens has a plurality of regions each of which is has a separate power output applied thereto so that the lens or eye protection device can have a non-uniform light transmission at a particular incident intensity of light. This permits the lens, for example when used in an eye protection device, to become darker in regions, such as at the top of the lens, and remain clearer at other regions, such as at the bottom of the lens. In the case of an eye protection device this permits a user to see without light attenuation when looking down and to have light attenuation when looking upwardly towards a source high intensity of light.

In another more particular aspect of the present invention the lens apparatus or eye protection device includes an electronic storage medium storing a plurality of power patterns for applying to the plurality of regions.

In another more particular aspect of the present invention the lens apparatus or eye protection device includes an electronic medium permitting an arbitrary plurality of power patterns for applying to the plurality of regions.

DETAILED DESCRIPTION

As is well known, unpolarized light is comprised of light in which the electric vector is randomly oriented; the direction of the electric vector is orthogonal to the direction of propagation of the light. Plane polarized light or linearly polarized light is light in which the electric vector generally is oriented in a single plane. Various means have been used in the past to polarize light, especially to convert unpolarized light to linearly polarized light.

With reference now to the drawings, particularly to FIG. 1, a device 10 according to the present invention is schematically shown. Device 10 is shown provided with a window or lens assembly 12 having an electro-optic light shutter 14. Device 10 has an electronic unit 16 that acts to vary the light transmission of electro-optic shutter 14. Electronic unit 16 incorporates a control 18 which permits manual, automatic, or both operations of device 10. Control 18 preferably permits either a manually operation, automatic operation or both operations of device 10. As will be seen, control 18 permits the electro-optic light shutter 14 to be substantially continuously varied or to be varied in finite steps from a substantially opaque to a maximum light-transmitting condition. In a preferred embodiment, device 10 is an eye protection device, in particular sun glasses. When device 10 is used as sun glasses, the light transmitivity of the light shutter 14 will vary as the ambient light conditions vary. The light transmitivity of the light shutter 14 will vary automatically in response to the ambient light conditions if the device 10 is in automatic mode or will vary in response to the user of the glasses manually controlling the light transmitivity if the device 10 if it is in manual mode of operation.

Electro-optic light shutter 14 most preferably comprises a liquid crystal light shutter hereinafter described with more particularity with reference to FIGS. 2, 3 and 4. However, the present invention is no limited to liquid crystal materials. For example, U.S. Pat. No. 3,245,315, the teaching of which is incorporated herein by reference, describes other types of electro-optic materials useful to practice the present invention.

Figure 2:
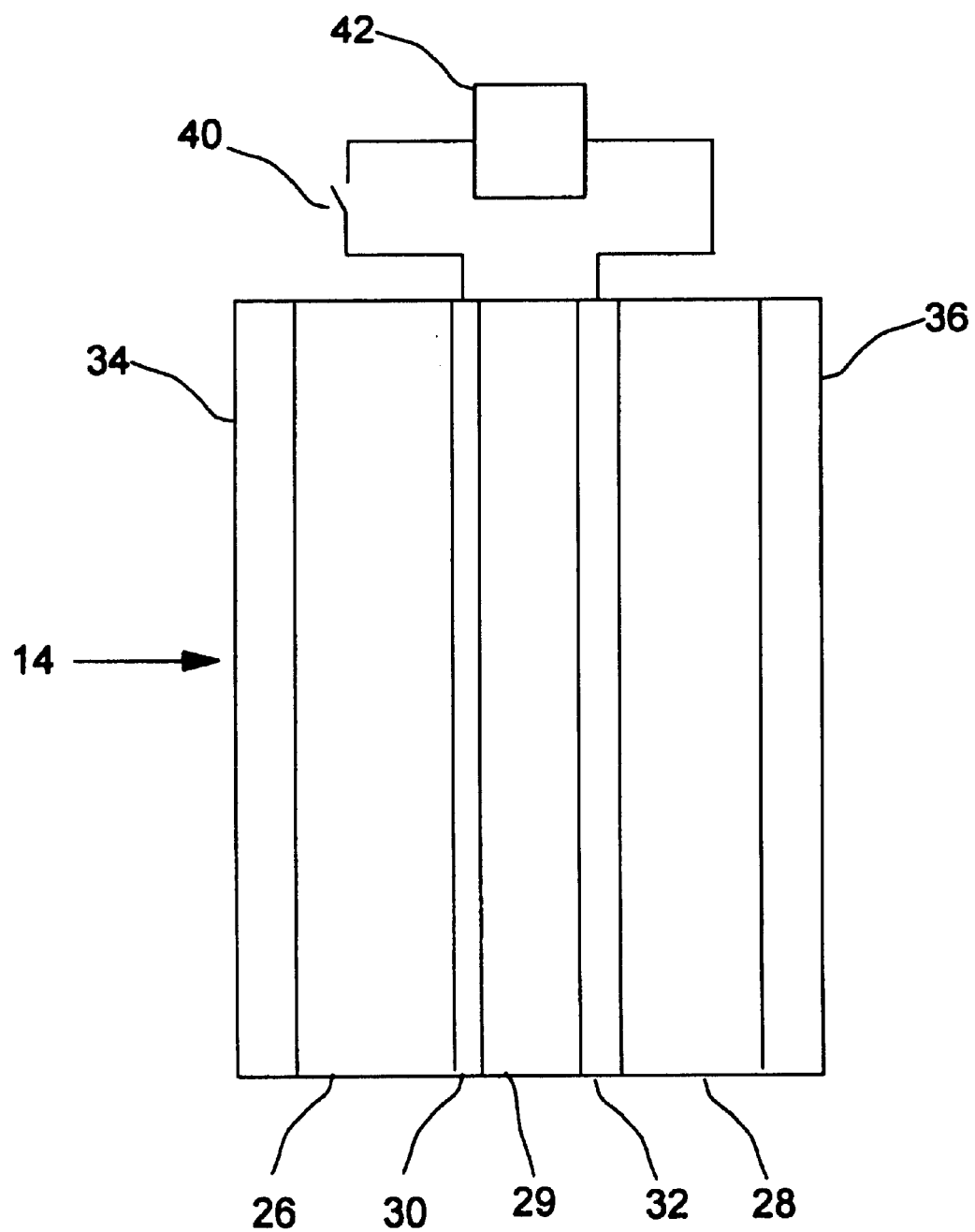
FIG. 2 is a schematic sectional view of a light shutter according to the present invention.

With reference to FIG. 2, the details of the liquid crystal shutter are shown. It comprises a first transparent plate 26, preferably glass, and a second transparent plate 28, also of glass, and extending spaced apart the plate 26. If plates 26 and 28 are substantially flat, they can be substantially spaced parallel to each other, as is, for example, shown in FIG. 2. In an embodiment the space between plates 26 and 28 is substantially uniform, as is, for example, shown in FIG. 2. However, the space does not have to be uniform. The teaching of U.S. Pat. 6,122,032, which teaches non-uniform spacing, is incorporated herein by reference. When this device 10 acts as lens which focuses or defocuses light, then the space between plates 26 and 28 may preferably not be uniform and plates 26 and 28 may not be planar but may have a curvature. The plates 26 and 28 are spaced apart by suitable spacers, not shown. U.S. Pat. Nos. 6,122,032,6,115,098, 4,763,995 and 5,513,026 teach spacers, the teachings of which are incorporated herein by reference. The space between the plates is filled with a nematic-phase liquid crystal material 29 with a positive dielectric anisotropy. A suitable nematic-liquid crystal material is described in U.S. Pat. No. 3918796 to Fergason, issued Nov. 11, 1975, the teaching of which is incorporated herein by reference.

A liquid crystal transmission shutter used in the present invention comprises a transmission mode system. The liquid crystal panel can be of conventional form, comprising two transparent plates of glass arranged spaced to one another and with a twisted nematic liquid crystal material separating the two plates. The two plates carry electrodes which define a row and column array of elements that are individually operable to modulate light whereby the light transmission through the panel is modulated to provide a transmission in accordance with digital information supplied to the panel, in conventional manner. Such a panel is described in U.S. Pat. Nos. 4,822,144 and 5,612,797, the teaching of which are incorporated herein by reference.

Disposed on the interior surfaces of the transparent plates 26 and 28 are coatings 30 and 32 of thin transparent electroconductive material, such as the known tin oxide, indium oxide coatings or electrically conductive polymers. The use of electrically conductive polymers as electrodes and electrical contacts is described in PCT publication WO 98/21755, published May 22, 1998, entitled PATTERNS OF ELECTRICALLY CONDUCTIVE POLYMERS AND THEIR APPLICATIONS AS ELECTRODES OR ELECTRICAL CONTACTS, the teaching of which is incorporated herein by reference. On the opposite sides of the two glass plates 26 and 28 are polarizers 34 and 36, these polarizers being polarized parallel to each other in the preferred embodiment of the invention.

U.S. Pat. No. 5,721,299, entitled "Electrically conductive and abrasion/scratch resistant polymeric materials, method of fabrication thereof and uses thereof", issued Feb. 24, 1998, teaches a combination of abrasion and scratch resistant material with electrically conductive polymers selected from the group of substituted and unsubstituted polyanilines, polyparaphenylenevinyles, substituted and unsubstituted polythiophenes substituted and unsubstituted poly-p-phenylene sulfides, substituted and unsubstituted polyfuranes, unsubstituted polyselenophenes, polyacetylines formed from soluble precursors, combinations thereof and rag blends thereof with other polymers. This patent also teaches coating of electrically conductive polymers with abrasion and scratch resistant polymers to provide enhance strength and environmental integrity to the electrically conductive polymers. The teaching of U.S. Pat. No. 5,721,299 is incorporated herein by reference.

Figure 3:
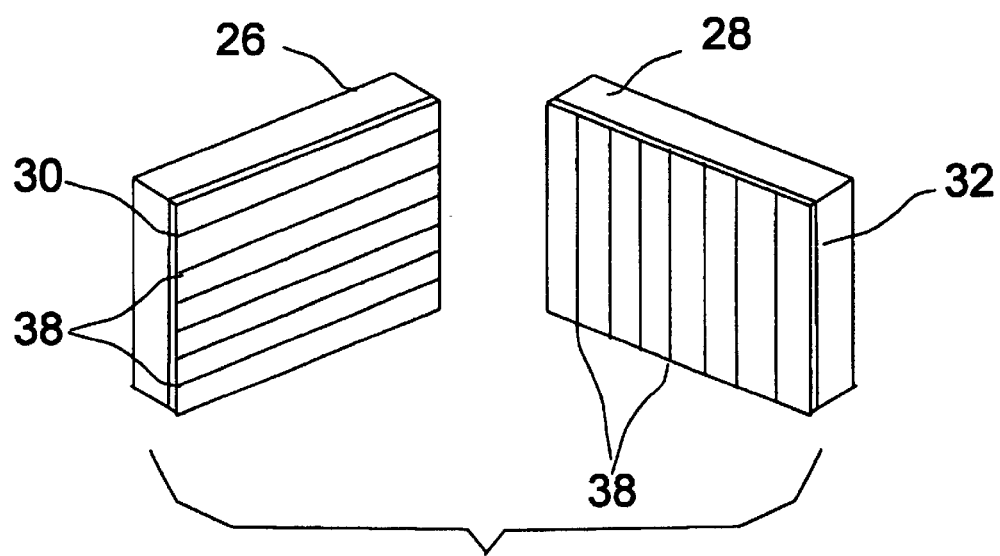
FIG. 3 is a view illustrating the manner in which the transparent plates of the liquid crystal unit of FIG. 2 are rubbed at right angles with respect to each other.

With reference to FIG. 3, in the preparation of the liquid crystal light shutter, the glass plates 26 and 28 with the transparent conductive coatings 30 and 32 thereon are prepared by initially rubbing them unidirectionally with, for example, a cotton cloth. The direction of rubbing on the respective plates 26 and 28 is indicated by the lines 38 and 39 in FIG. 3; and it will be appreciated that, in a preferred embodiment, the directions of rubbing on the respective plates are at right angles to each other. The effect of this is to produce a twisted nematic structure. In this respect, the molecules in the nematic-phase liquid crystal material are each long and straight, and they tend to lie parallel with respect to one another, like logs in a river or straws in a broom. They are free to move with respect to one another, and there are some that are at a small acute angle with respect to the "main stream" and a few others that are at any given moment in a position even less consonant with the bulk of the others. A property of the nematic-phase liquid crystal material is that the molecules in the vicinity of a rubbed surface tend to align themselves. Thus, the molecules nearest the surface of the plate 26, for example, are inclined to orient themselves with their long axes parallel to the lines 38 and those nearest the surface of plate 28 are inclined to orient themselves with their long axes parallel to the lines 39. In-between the rubbed surfaces, a twisted structure results; and the effect of this twisted structure on polarized light is to rotate it through 90°. If, however, a potential is applied between the transparent conductive films 30 and 32 as by closing switch 40 (FIG. 2) to apply the potential of variable voltage source 42 across the liquid crystal layer 29, the molecules will no longer be parallel to the rubbed surfaces 38 but rather will be normal thereto. This destroys the twisted structure; and the polarized light will no longer be rotated through 90° in passing through the liquid crystal cell. Liquid crystal layer 29 can be any type of liquid crystal material and material 29 can be any electro-optic material.

The effect of the light shutter on polarized light parallel to the lines 38, for example, is that the unit effects a rotation of the plane of polarization of the light as it passes there through so that the light emanating from the surface of plate 28 is plane polarized parallel to the lines 39. However, it would not matter if the plane polarized light impinging upon the plate 26, for example, were polarized at some angle with respect to the lines 38. The same effect of rotation of the plane of polarization is obtained. The extent of rotation does not need to be 90°. Any desired extent of rotation may be obtained, merely by properly orienting the unidirectionally rubbed surfaces on the plates 26 and 28. However, when the directions of rubbing are at right angles to each other, the extent of rotation is 90°.

Figure 4:
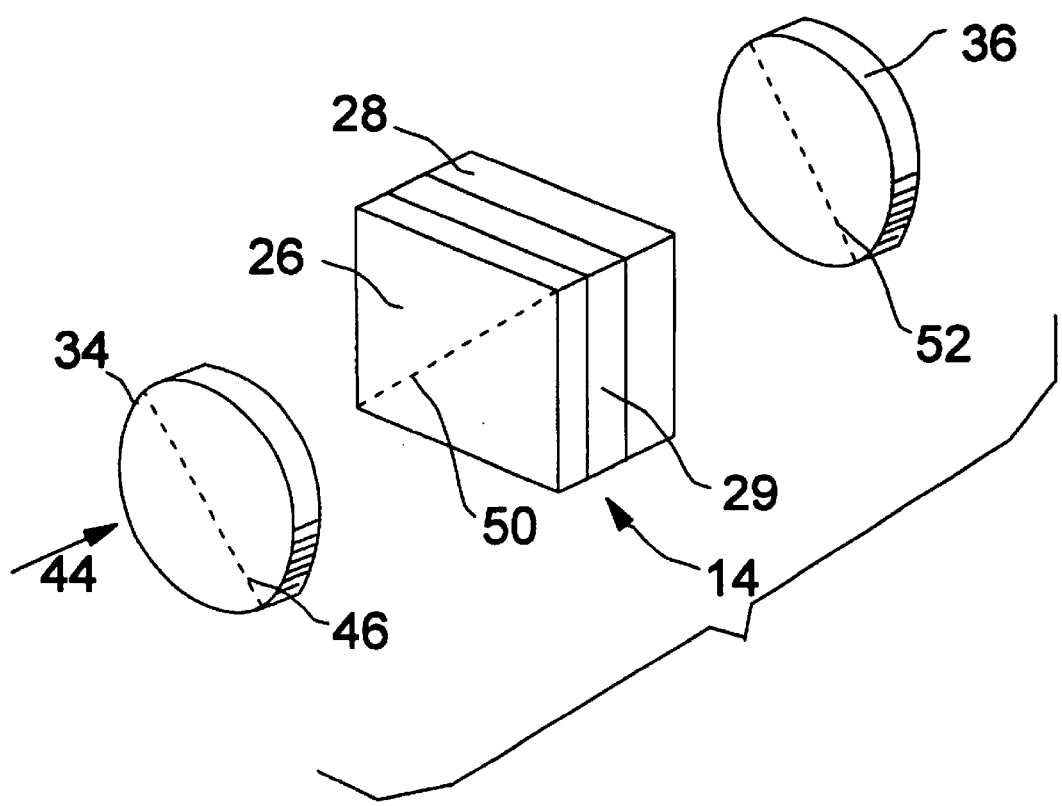
FIG. 4 is a schematic illustration showing the manner in which polarized light passes through the liquid crystal unit of the lens assembly of FIG. 2.

The effect of the liquid crystal unit of FIG. 2 on polarized light is schematically illustrated in FIG. 4. Thus, a source of unpolarized or natural light at 44 impinges on the polarizer 34 which polarizes the light in a plane indicated by the broken lines 46. This polarized light, as it passes through the liquid crystal shutter indicated by the reference numeral 14, such as the unit shown in FIG. 2, will be rotated through 90° so that the polarized light is then polarized in a plane indicated by the broken lines 50. If the polarizer 36 passes polarized light in the plane indicated by the broken lines 52, it can be seen that since the plane of polarization of the light emanating from the unit 14 is at right angles to the plane of polarization of the polarizer 36, no light will pass through and the light shutter will be opaque, or substantially opaque on the order of less than 1% light transmission. The amount of flight transmission, however, can be adjusted by rotating either polarizer 34 or polarizer 36.

Now, if an electrical potential is applied across the transparent conductive films 30 and 32 of the light shutter 14, polarized light will no longer be rotated through 90° in passing through the unit. As a result, the polarized light will pass through each of the polarizers 34 and 36 as well as the light shutter 14 and the light shutter will be light-transmitting.

It will be appreciated that by shifting the plane of polarization of polarizer 36 such that it is at 90° to the plane of polarization of polarizer 34, the operation of the device will be reversed. That is, with no potential applied across the transparent conductive films, the polarized light will still be rotated through 90° and will pass through polarizer 36. On the other hand, when a potential is applied and the polarized light is no longer rotated in passing through the cell 14, polarizer 36 will block the light.

Figure 5:
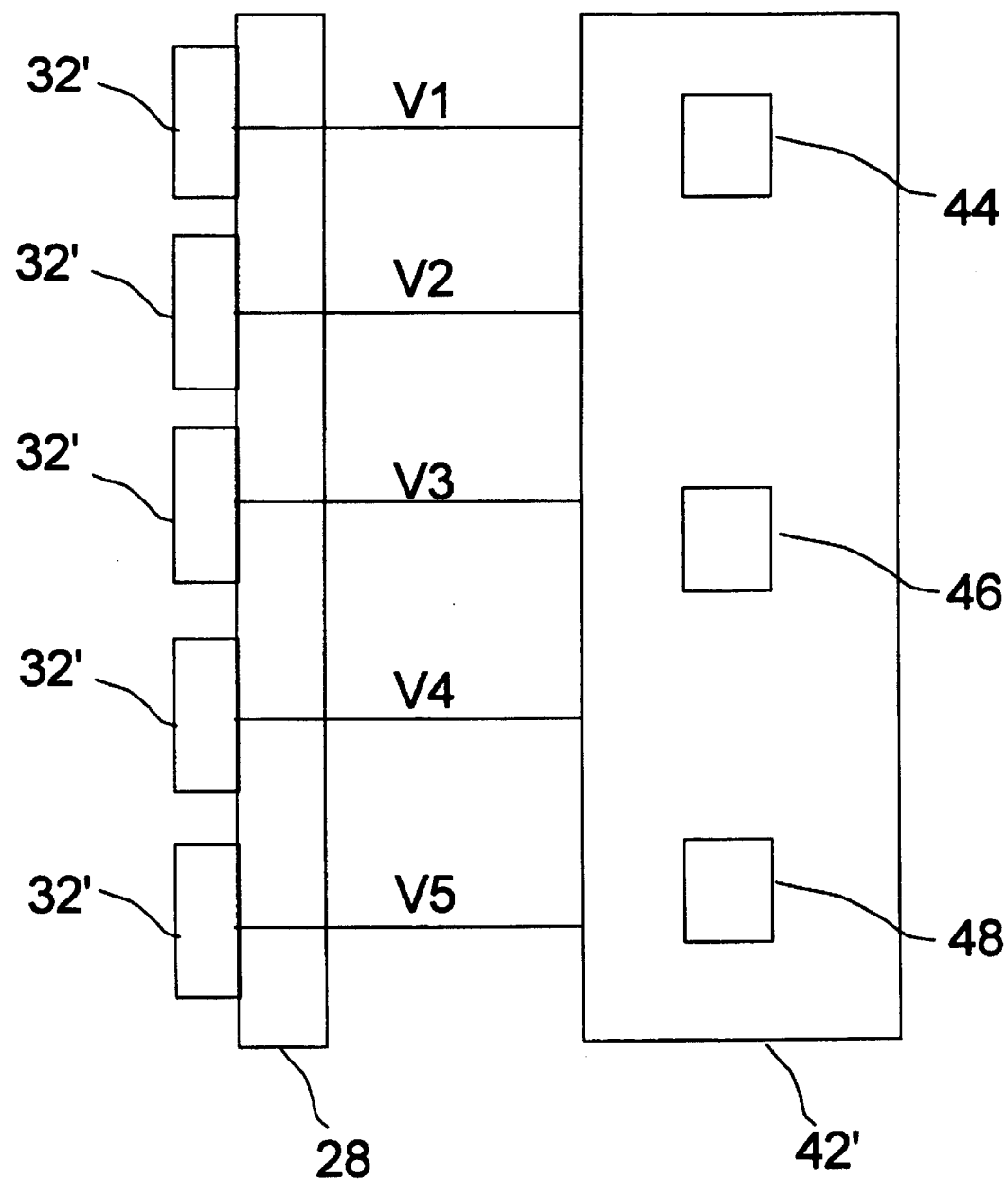
FIG. 5 schematically shows a portion of the light shutter of FIG. 2 having a pattern of conductive regions permitting a non-uniform voltage to be applied to the light shutter to result in non-uniform transmission of light through the light shutter.
Figure 6:
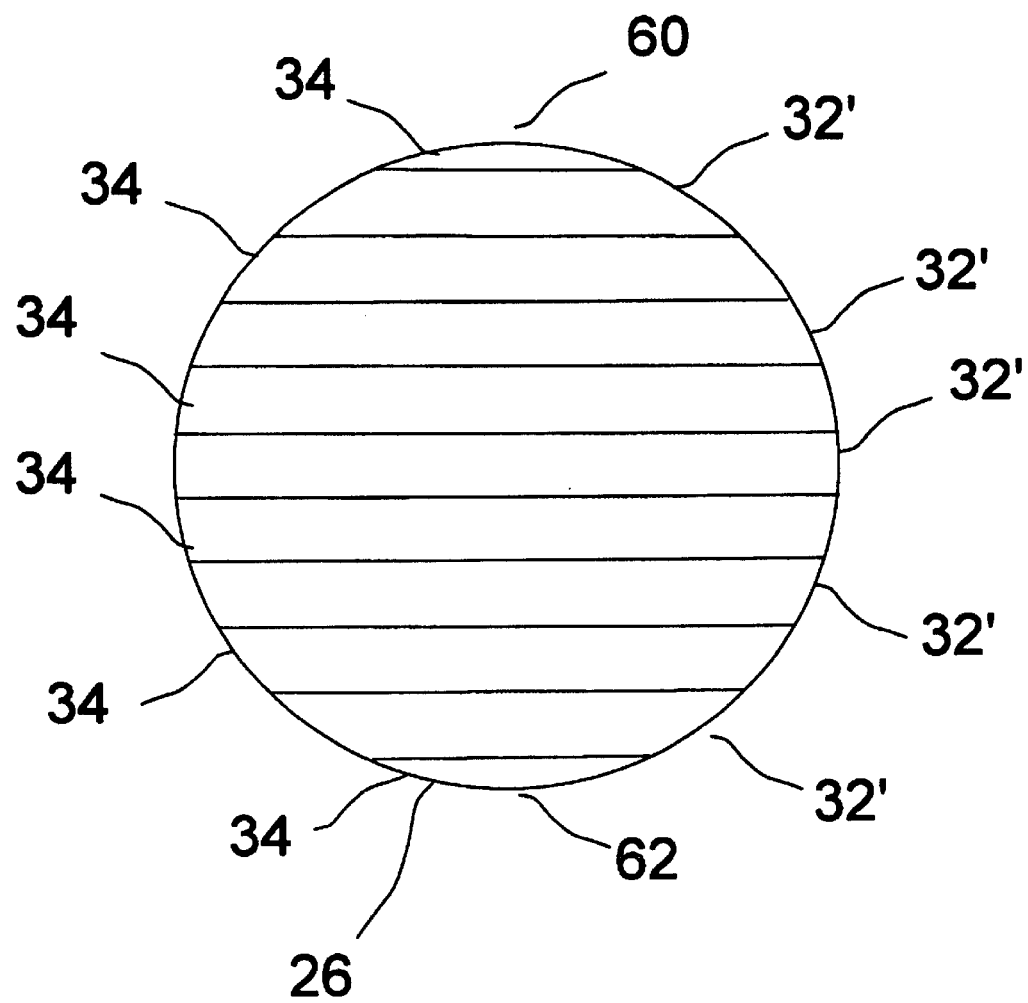
FIG. 6 shows a front view of the portion of the light shutter shown in FIG. 5.

FIG. 5 shows a schematic view of glass plat 28 of FIG. 2 wherein the continuous conductive layer 32 is replaced by a patterned conductive layer 32'. FIG. 6 is a front view of glass plate 26 showing the regions. 32' as stripes of conductive material 32' across the surface of the plate 26. As schematically shown in FIG. 5 each of the conductive stripes 32' has a separate voltage output V1 to V5 applied thereto. (FIG. 5 shows five voltages V1 to V5 only for purposes of example. There are as many voltage outputs as there are electrodes 32' to which to apply voltages.) Thus the optical transmission of light shutter 14 of FIG. 2 can be controlled to be nonuniform non-uniform between the top 60 and the bottom 62 of the light shutter 14. Therefore, a user of the eye protection device according to the present invention can manually control, such as by a manual control 44, the variable voltage source 42' of FIG. 5 to adjust the degree of optical transmission across the light shutter 14. Alternatively, variable voltage source 42' can have a light sensitive control 46 (such as a phototransistor) which can sense the incident light and in response to the intensity cause variable voltage source 42' to output different voltage values to voltage outputs V1 to V5 so that the optical transmission through the light shutter 14 is different in different regions. Alternatively, the variable voltage source 42' can be controlled by a electronic device 48, such as a semiconductor chip, to provide stored voltage patterns which can be selected by a user for different lighting conditions. For example, a user may desire a different light transmission pattern in response to the same light intensity in different environments, such as at the beach as compared to a city.

Figure 7:
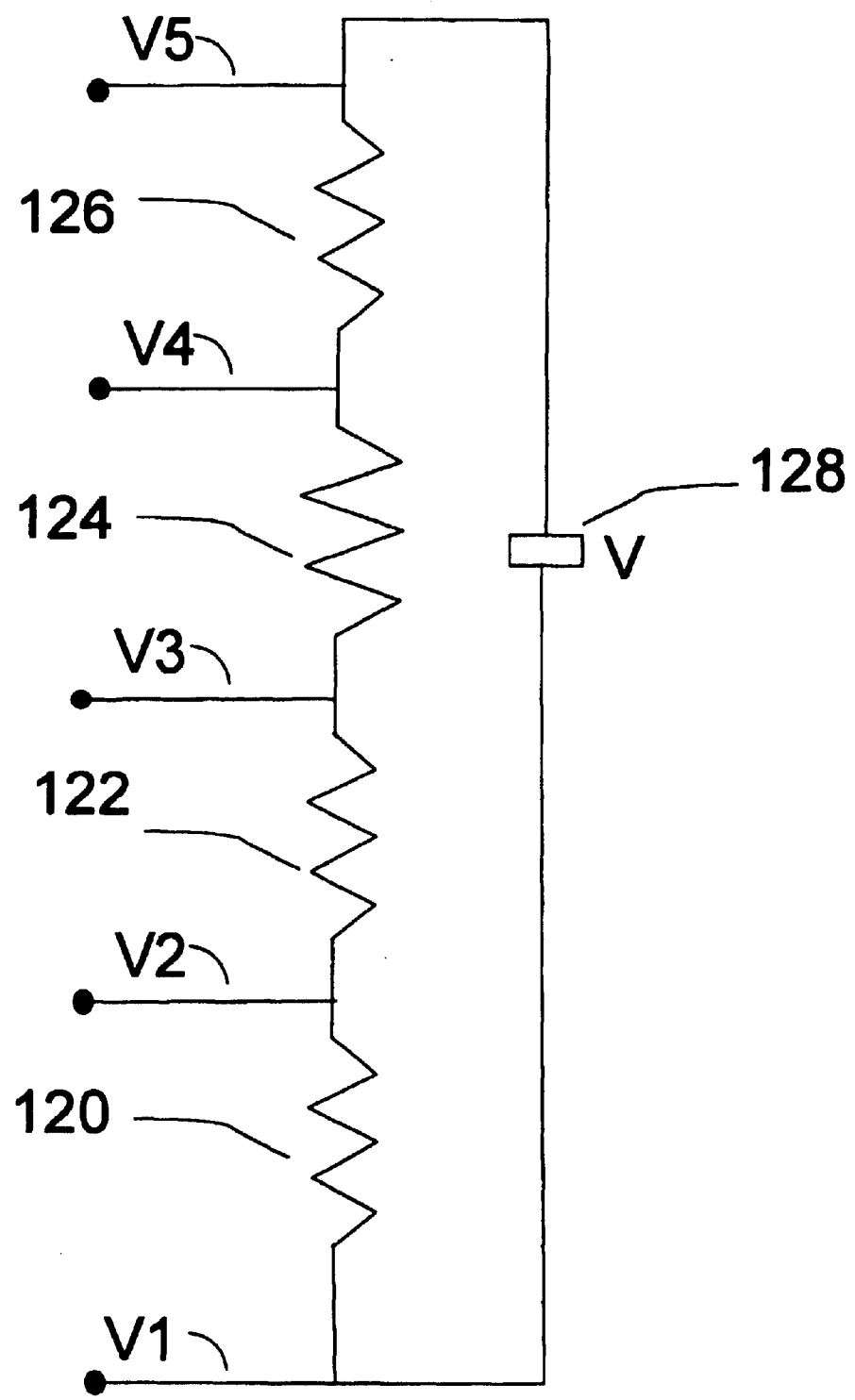
FIG. 7 schematically shows a pair of eye glasses implementing the present invention.

FIG. 7 schematically shows an example of a variable voltage source 42 or 42' that comprises a ladder of resistors 120, 122, 124, and 126 that can have equal or different values. A variable voltage source 128 is applied over the resistor ladder to generate voltages V1, V2, V3, V4, and V5. More complex patterns of output voltages can be generated using an integrated circuit chip, for example, of the type referred to a a data drive, such as a LCD Controller/Driver such as described in the Hitachi e Controller/Driver LSI Data Book, in particular, integrated circuit chip HD66330TLCD. Using such an integrated circuit chip a digital input corresponds to a voltage out put of a particular amount. Thus the system can be designed so that the user can select a particular set of digital inputs to be applied to generate a desired set of output voltages for a particular transmitivity pattern through the electro-optic shutter 14. The transmission through the electro-optic shutter 14 at a particular location of the electro-optic shutter 14 depends on the voltage applied at that location. The input digital pattern corresponding to the output voltage pattern can be preset so that only one pattern is available or the user can have a choice of a number of patterns, so that a different transmitivity pattern can be selected by the user.

Figure 8:
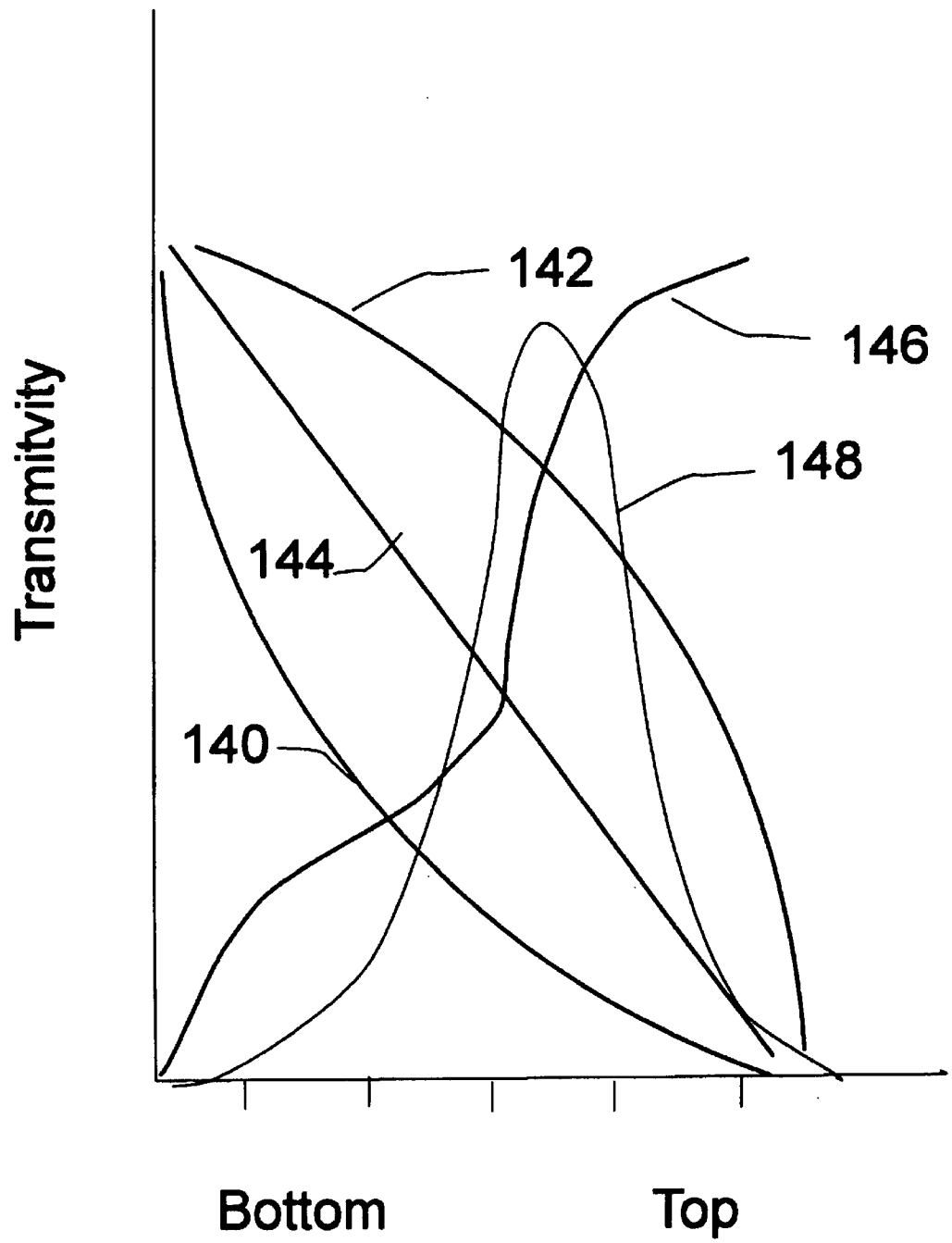
FIG. 8 schematically shows an example of a variable voltage source that comprises a ladder of resistors.

FIG. 8 schematically shows exemplary plots 140, 142, 144, 146 and 148 of transmitivity verses the distance from the top to the bottom of the electro-optic shutter 14 as shown in FIG. 6. The plots can have any shape.

Figure 9:
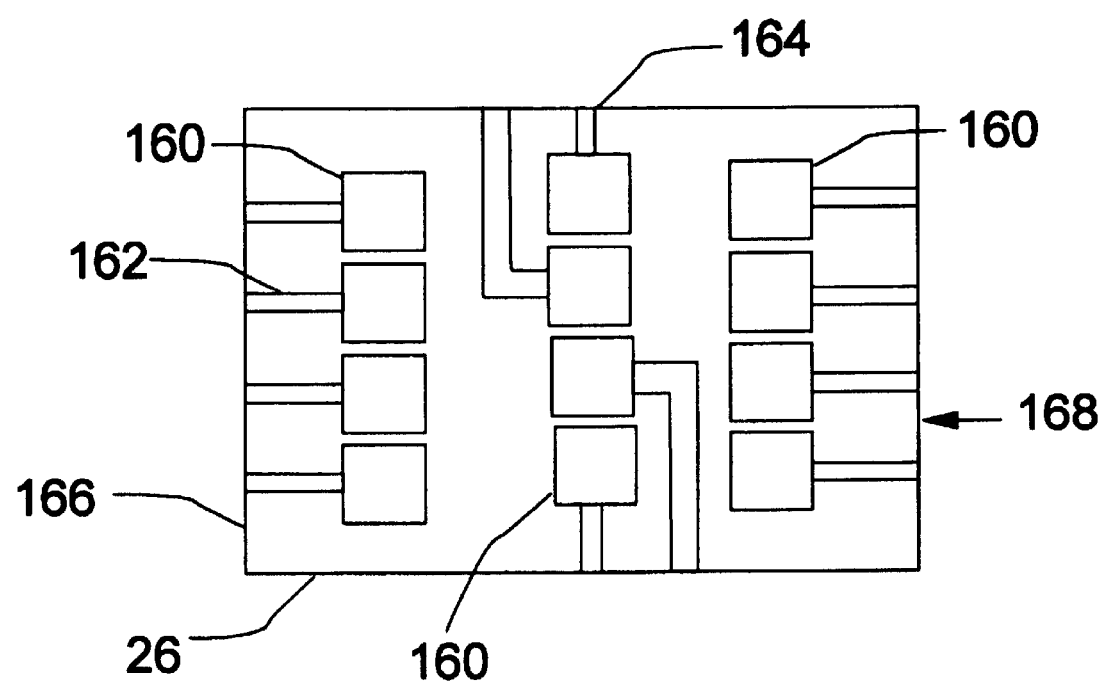
FIG. 9 schematically shows exemplary plots of transmitivity verses the distance from the top to the bottom of the electro-optic shutter.

FIG. 9 schematically shows an alternative embodiment of the electro-optic shutter (or lens) 168 to the electro-optic shutter or lens 14' of FIG. 6. . Rather than having conductive stripes 32 spanning across the transparent substrate 26 as in FIG. 6, transparent substrate 26' of FIG. 9 has a plurality of preferable transparent el electrically conductive lines 162 to provide an electrical connection from conductive regions 160 to edge 166 of transparent substrate 26'. A different amount of power, for example a voltage or current can be applied each region 160 so that the transparency in each region can be different.

Figure 10:
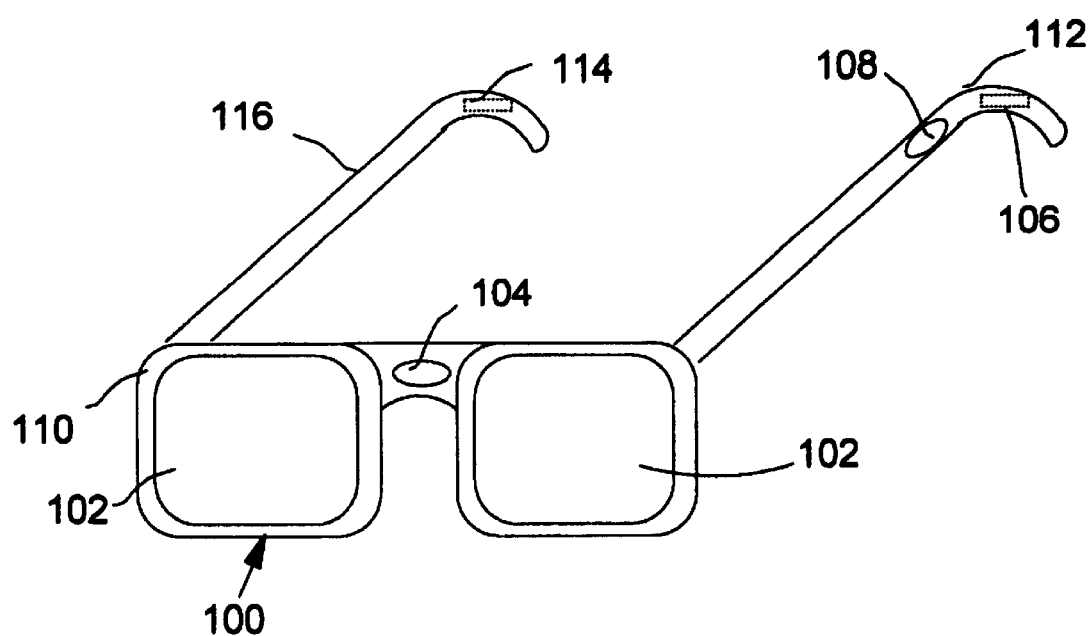
FIG. 10 schematically shows an alternative embodiment of the electro-optic shutter.

The electro-optic shutter or lens 14 can be a single color or multicolored or of variable color. U.S. Pat. No. 5,680,187, entitled "Liquid Crystal Display Device And Method For Manufacturing the Same", the teaching of which is incorporated herein by reference, teaches colored transmission liquid displays for display screens. As is well known in the art of liquid crystal displays, The electro-optic shutter or lens 14 can have a different color depending on the selection of the user. The electro-optic shutter or lens 14 is segmented into pixels, each of which has in a preferred embodiment a red, green and blue region so that FIG. 10 schematically shows a pair of eye glasses 100 implementing the present invention.

Eye glasses 100 have frame 110 and two lenses 102. Lenses 102 can have a single power controlled region or a plurality of power controlled regions as taught herein. The power can be provided by a power source 106, such as a battery, stored in side piece 112 or stored elsewhere in the eye glass frame or outside the eye glass frame. The power is applied to the lenses 102 by means of a photosensitive region 104 or a manual switch 108. A photosensitive region, such as a phototransistor, is taught in U.S. Pat. No. 3,245,315, entitled "Electro-Optic Responsive Flash Blindness Controlling Device", the teaching of which is incorporated herein by reference and a photosensitive region is taught in U.S. Pat. No. 5,276,539, entitled "Method and Apparatus For controlling Perceived Brightness using a time varying shutter", the teaching of which is incorporated herein by reference. A manual switch 108, for example, can be a roll switch or a slide switch that is used to vary the power applied to the lenses 102. Roll switches and slide switches are commonly available in the art. In addition, the eye glasses 100 can be electronically controlled, such as being under a CPU control, as described above, using for example a semiconductor chip 114 stored in side piece 116 or in or on any part of the frame of the eye glasses or it can be external to the eye glass frame. The semiconductor chip can store different power application patterns for providing different light transmission responses to the lenses 102 and different color to the lenses 102. Each lens 102 can have a different pattern and a different color.

The time varying control as taught in U.S. Pat.No. 5,276,539, entitled "Method and Apparatus For controlling Perceived Brightness using a time varying shutter", the teaching of which is incorporated herein by reference, can be applied to regions 32' of FIG. 6 and to regions 160 of FIG. 9 to create the apparent effect of a change in brightness from the top to bottom of the lens in FIG. 6 or in any arbitrary pattern as in FIG. 9.

Figure 11:
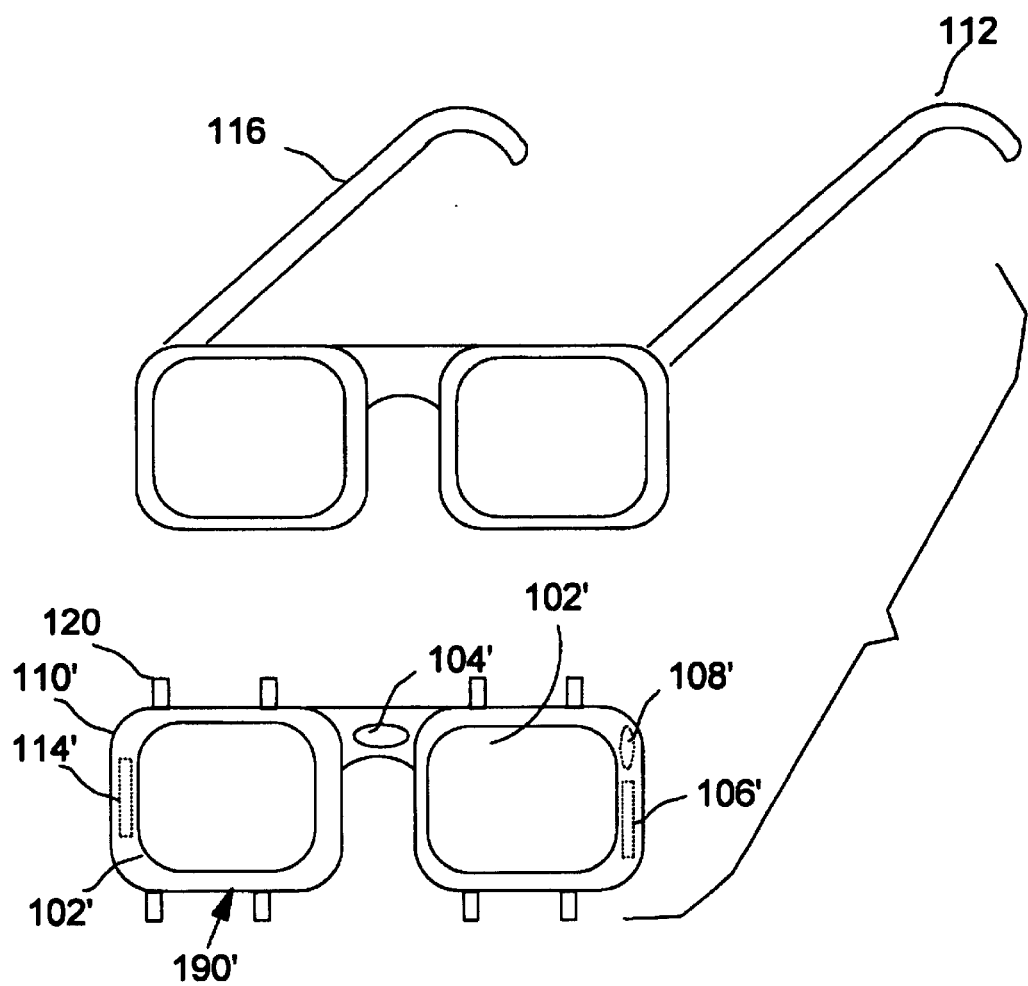
FIG. 11 is a schematic diagram of a pair of eye glasses and a clip on eye shade device.

FIG. 11 is a schematic diagram of a pair of eye glasses 180 and a clip on eye shade device 190. Primed numbers in FIG. 11 correspond to and represent the same components as the corresponding unprimed numbers in FIG. 10. Eye glasses 180 has two lens 182 which can be prescription lenses. Clip on eye shade device 190 has clips 120 to hold device 190 onto frame 192 of eye glasses 180.

Figure 12:
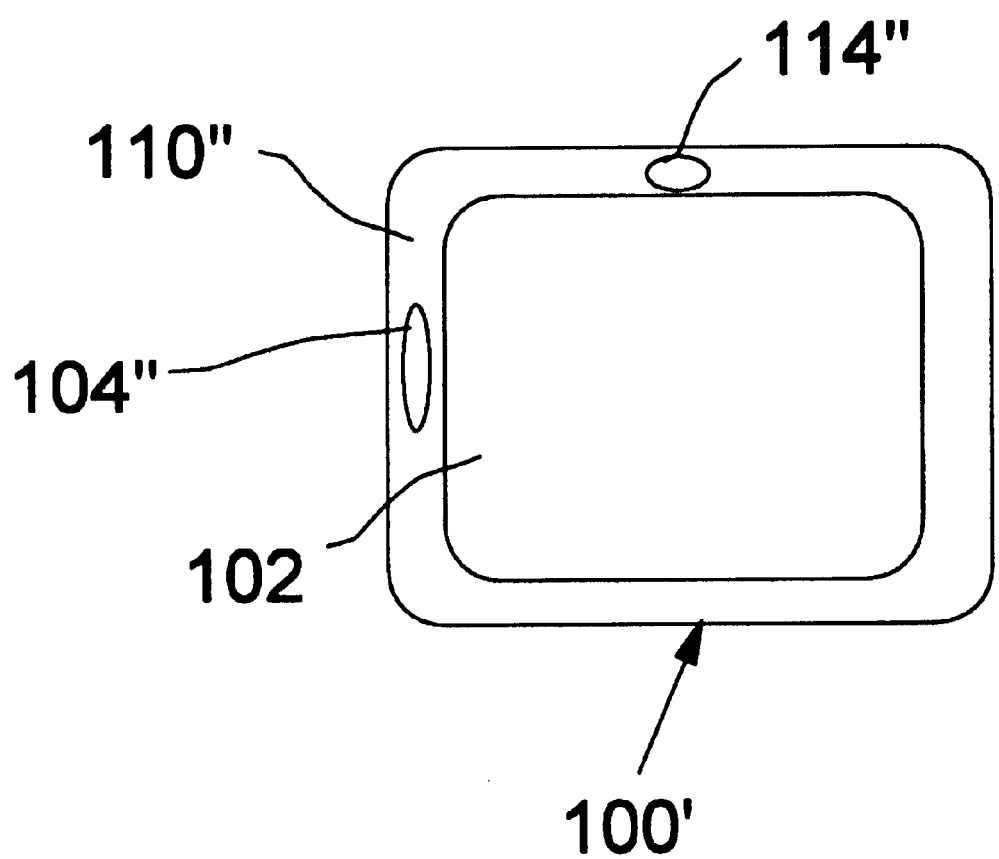
FIG. 12 is a schematic diagram of one of the lenses 100 of FIG. 10, which has a separate brightness control.

FIG. 12 is a schematic diagram of one of the lenses 100 of FIG. 10 designated as 100'. Lens 100' has a separate light sensitive region 114" to control the response of the individual lens. Thus both lenses 100 of FIG. 10 can have a separate response to the incident light intensity. Therefore, each lens can have a different light transmission pattern. Also, lens 100' can have a separate manual control 104", so that each lens 100 of FIG. 10 can be adjusted to have a different color of different light transmission pattern.

Figure 13:
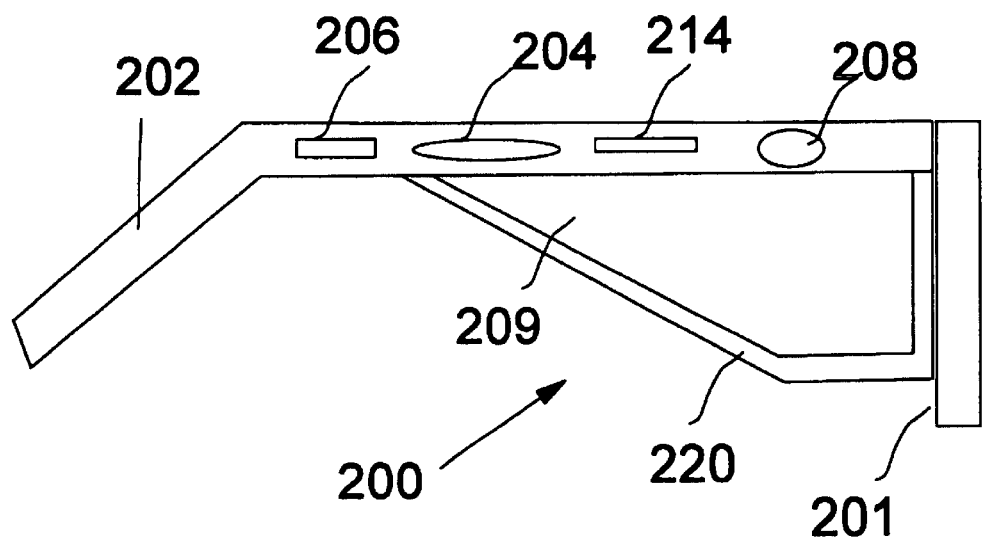
FIG. 13 is a schematic diagram of a side view of an eye shade device that has side lenses.

FIG. 13 is a schematics diagram of a side view of an eye shade device 200 which can have a front view as shown in FIG. 10. The front face 201 of eye shade device 200 can correspond to frame 100 of FIG. 10 which comprises the two lenses 102. Side piece 202 corresponds to side piece 116 of FIG. 10. Light sensitive region 204 corresponds to light sensitive region 104 of FIG. 10. Power source 206 corresponds to power source 106 of FIG. 10 . Microprocessor 214 corresponds to microprocessor 114 of FIG. 10. Manual control 208 corresponds t manual control 108 of FIG. 10. Elements 204, 206, 208 and 214 are optional since the function that each corresponds to can be provided by one set of these functions for the entire eye shade device 200. Side piece 202 has attached to it subframe 220 that frames side lens 209. (There are two side frames and side lenses, one on each side of the front lens assembly 201. Optionally, each lens 102 and 209 can have its own photosensitive region, microprocessor, power source, and manual switch. Thus each lens can have a different transmitivity pattern which depends either on the user choice in the case of manual control or in the case of automatically controlled by the photosensitive regions 114, 114' and 204 so that each lens 102 and each side lens 209 can have a different transmitivity pattern depending on the intensity of the light incident on each lens separately. A particular use of the eye shade device 200 is for driving an automobile wherein it is common for the light intensity, during certain times of the day, to be very intense on one side of the automobile and not in the front ahead direction. In such an instance it is desirable for the incident light to be more heavily attenuated from the side which is facing the incident light. Thus on of the side lenses 209 would be very dark as compared to the other side lens 209 and as compared to the two front lenses 102.

Figure 14:
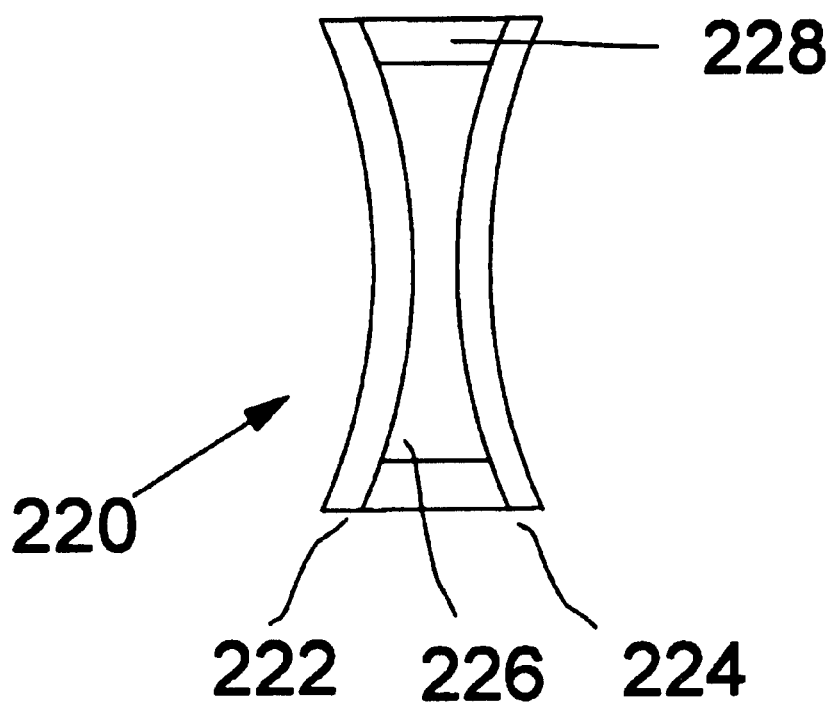
FIG. 14 and FIG. 15 are schematic diagrams of light shutters such as shown in FIG. 2 wherein the thickness of the light shutter is non-uniform.
Figure 15:
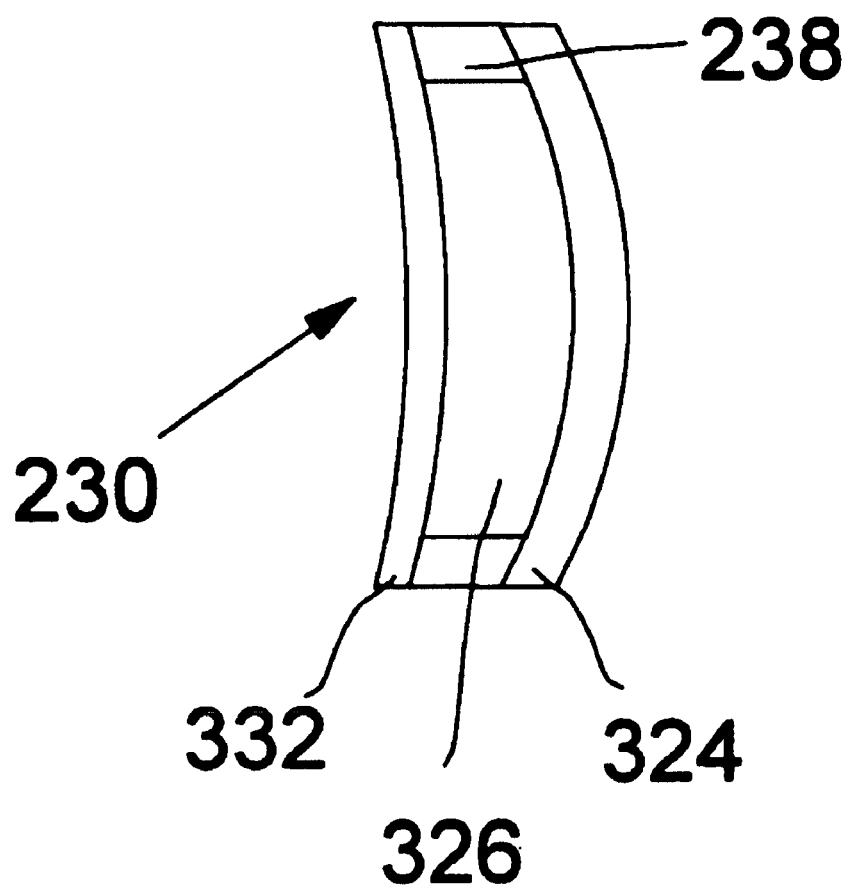

FIG. 14 and FIG. 15 are schematic diagrams of light shutters such as shown in FIG. 2 wherein the thickness of the light shutter is nonuniform. In one example region 226 of FIG. 14 and region 326 of FIG. 15 may corresponds to region 29 of FIG. 2, region 222 of FIG. 14 correspond to regions 34, 26 and 30 of FIG. 2; and 224 region of FIG. 14 corresponds to regions 36, 28 and 32 of FIG. 2. FIG. 14 shows spacer 228 to space regions 222 and 224 apart. FIG. 15 shows spacer 326 to space regions 332 and 324 apart. Since the lenses in FIGS. 14 and 15 have nonuniform thickness they can act as focusing lenses, whereas the lens 14 of FIG. 2 is planar and commonly available structures of this type typically do not have any significant focusing effect. Liquid crystal devices of varying thickness are taught in U.S. Pat. No. 6,122,032, entitled "Wedge Shaped LCD With Changes In Dispersion density of Spacers", the teaching of which is incorporated herein by reference.

Figure 16:
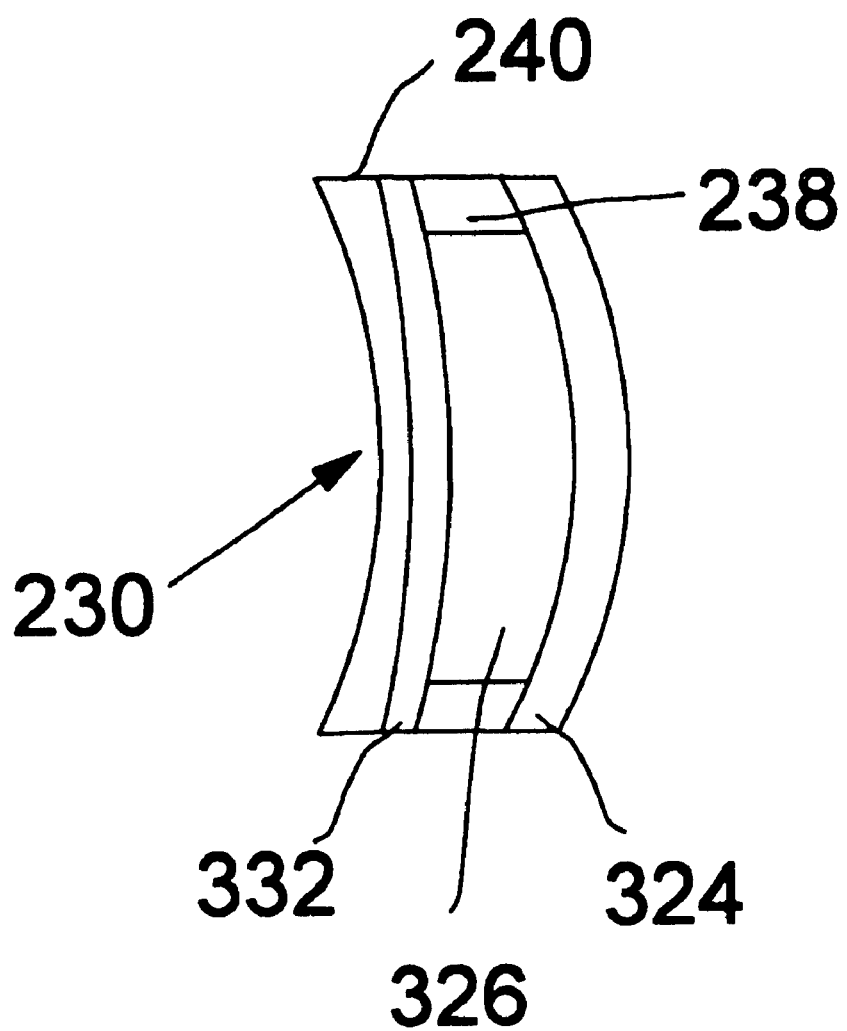
FIG. 16 schematically shows a a light shutter according to the present invention disposed on a focusing lens 240.

FIG. 16 schematically shows a a light shutter according to the present invention disposed on a focusing lens 240. FIG. 16 shows the device of FIG. 15 mounted on surface 242 of focusing lens 240 that can be done using commonly available optical adhesive. The focusing lens can be any prescription lens or nonprescription lens. Alternatively, the structure of FIG. 2 can be fabricated directly on lens 240 with the lens 240 serving as the transparent substrate on which the remaining layers as shown in FIG. 2 are disposed.

Figure 17:
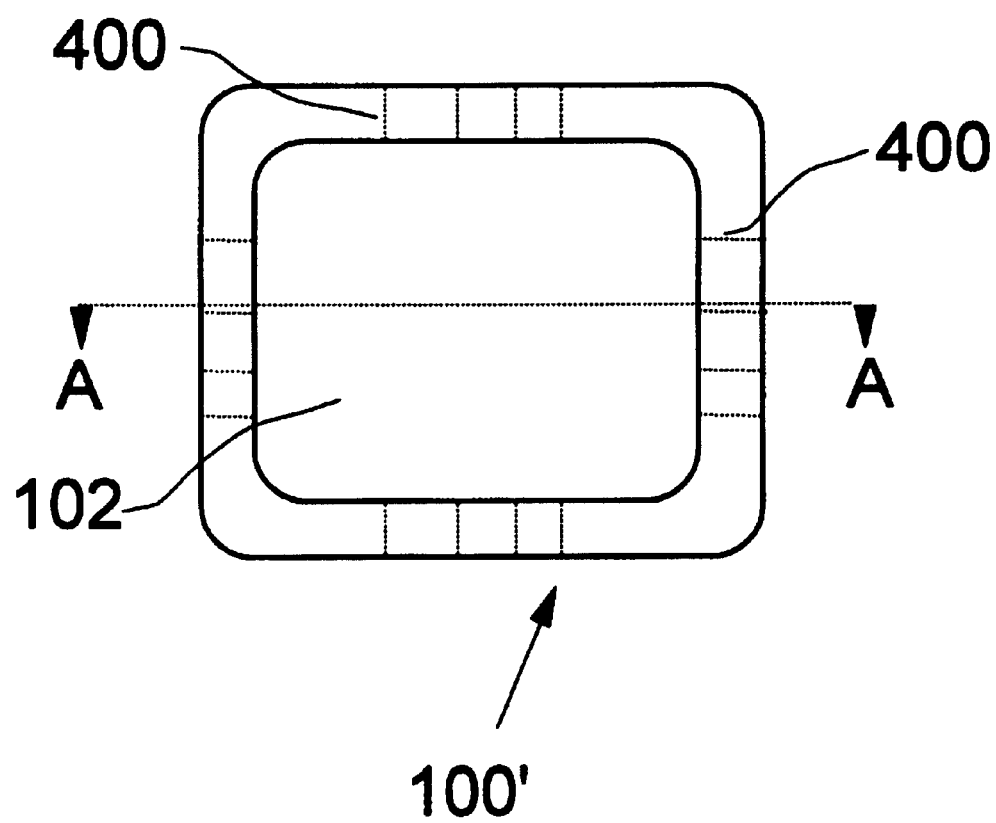
FIG. 17 is the same view as FIG. 12 wherein the lines 400 in phantom corresponds to electrical interconnections within frame 110.
Figure 18:
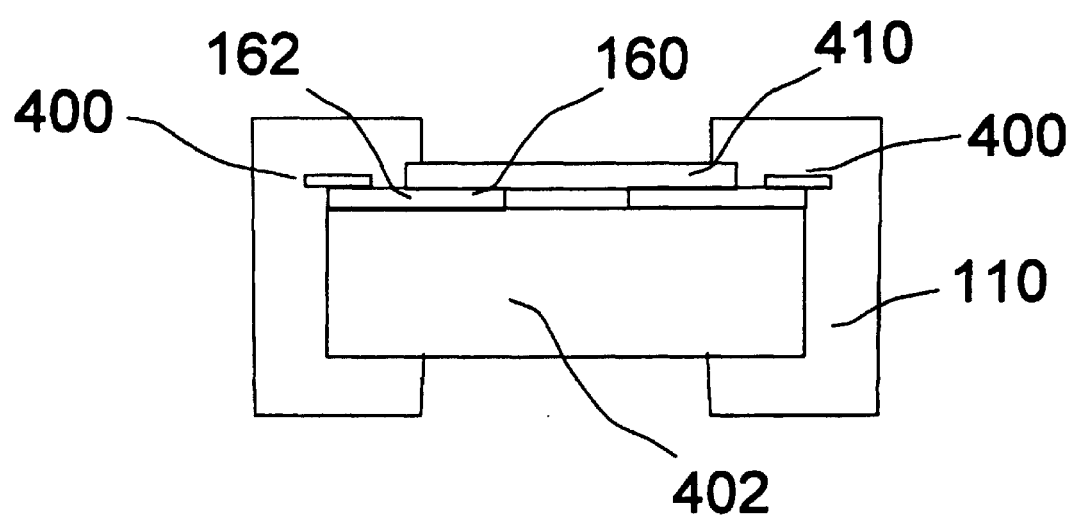
FIG. 18 is a schematic view along the line AA of FIG. 17.

FIG. 17 is the same view as FIG. 12 wherein the lines 400 in phantom correspond to electrical interconnections within frame 110. FIG. 18 is a schematic view along the line AA of FIG. 17 that passes through two electrical interconnections 400. The electrically conductive regions 160 (see for example FIG. 9) are electrically connected through electrically conductive lines 162 (see for example FIG. 9) to electrical conductors 400 embedded in frame 110. The frame 110 of FIG. 12, the side pieces 116 of FIG. 10 and the frame 220 of FIG. 13 can be made according the methods of fabricating printed circuit boards to form electrical conductors embedded in a dielectric material, with, if necessary, electrically conductive vias reaching the surface of the frame 110, the side pieces 116 and the frame 220. Thus electrical interconnection between the microprocessor, switches and power sources can be readily made using know principles of printed circuit board fabrication, such as is described in U.S. Pat. No. 4,606,787, which issued on Aug. 19, 1986 to Pelligrino, entitled "Method and Apparatus For Manufacturing Multi-Layer Printed Circuit Boards," the teaching of which is incorporated herein by reference. In FIG. 18 region 402 corresponds to all layers in FIG. 2 except for the either the electrically conductive layer 26 or 28 and one of the polarizers 34 or 36 which in FIG. 18 correspond to layer 410. The structure and the sequence of layers are exemplary only and not limiting. Any electo-optic structure, e.g., liquid crystal can be used.

Figure 19:
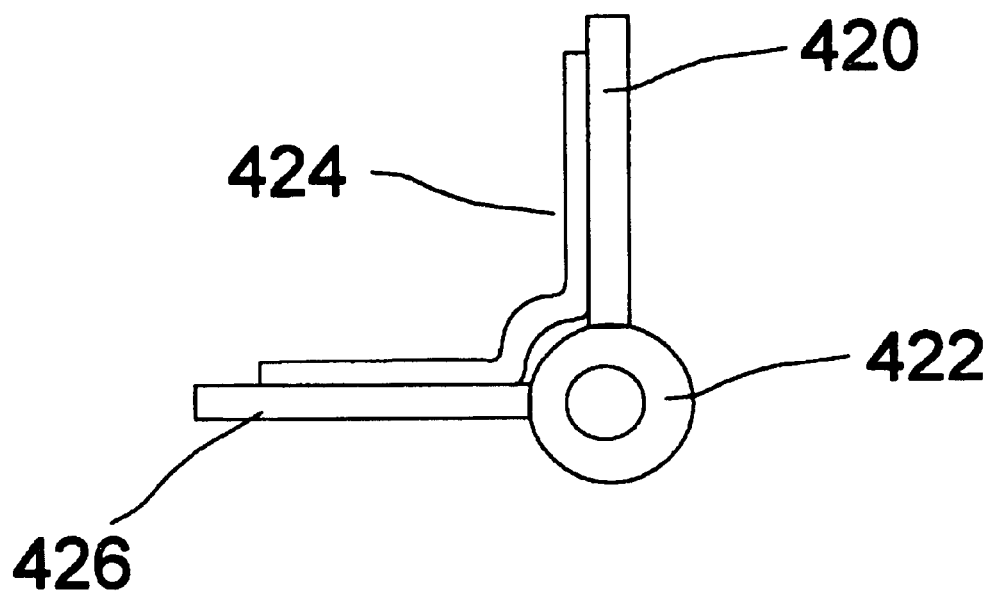
FIG. 19 schematically shows a hinge 422 between, for example between 110 (420 or 426) and side piece 116 (420 or 426) of FIG. 2.

FIG. 19 schematically shows a hinge 422 between, for example frame 110 (420 or 426) and side piece 116 (420 or 426) of FIG. 2. Flex tape 424 is disposed on the surface of 420 and 426 and bridges over hinge 422. Flex tape (or TAB tape) is typically a polymer film one or more layers of a flexible polymer film with one or more layers of patterned electrical conductors. The Flex or TAB tape provides a means for electrical interconnection of electrical components. This is as an alternative to or is in addition to electrical conductors embedded in the frame 100 and side pieces 116. Flex tape and methods of fabrication thereof are described in U.S. Pat. No. 5,045,921 issued Sep. 3, 1991, entitled "Pad Array Carrier Device Using Flexible Tape," the teaching of which is incorporated herein be reference. Alternatively, electrical connections can pass through the hinge as is commonly used in the art, in particular the electrical connections that connect a laptop PC keyboard section to the fold down display section that is physically and electrically connected to the keyboard section through a hinge.

U.S. Pat. No. 5,681,176, entitled "Hinge connector suitable for use in a hinge portion included in an electronic device" to Ibaraki et al., issued Oct. 28, 1997 and U.S. Pat. No. 5,237,488, entitled "Portable computer with display unit connected to system unit through conducting hinge", to Moser et al issued 8/1993, are directed to hinges for providing electrical connection between two parts of an electronic apparatus connected by a hinge. The teaching of U.S. Pat. Nos. 5,681,176 and 5,237,488 are incorporated herein by reference.

Figure 20:
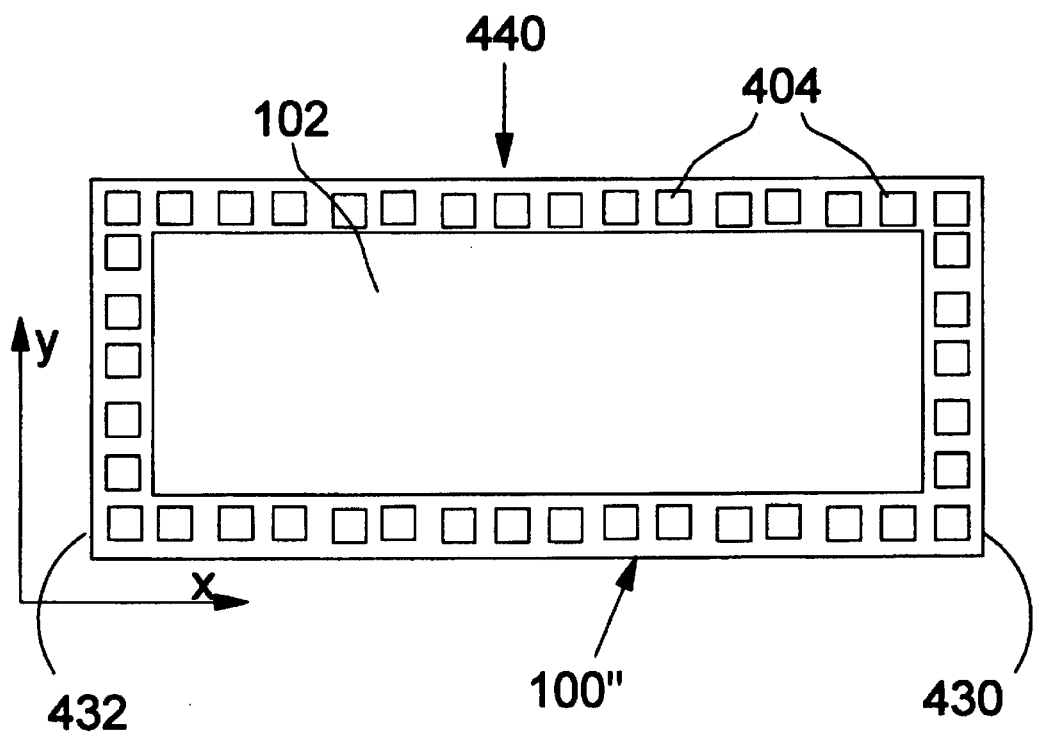
FIG. 20 is another embodiment of a shutter, for example such as shown in FIG. 12, having a plurality of light sensitive regions 404 disposed around the periphery of the shutter 100".

FIG. 20 is another embodiment of a shutter, for example such as shown in FIG. 12, having a plurality of light sensitive regions 404 disposed around the periphery of the shutter 100". If the lens 102 has the configuration of FIG. 6, the light sensitive regions control the power applied to the conductive lines 32'. One light sensitive region 404 may corresponds to one or more of the line 32', If the lens 102 has the configuration of FIG. 9, the light sensitive regions 404 corresponds to one or more of the electrically conductive regions 160 controlling the power applied thereto. Alternatively, the light (or any wave length of electromagnetic radiation whenever the term light is used herein it includes any wavelength of electromagnetic radiation) incident on each of the light sensitive regions forms a radiation intensity boundary condition at the periphery of the shutter 100" corresponding the x-y coordinates of the light sensitive regions. From this boundary condition a distribution of power outputs, e.g. voltage outputs, can be determined to apply to the plurality of electrically conductive lines 162 and regions 160. This can be done by the electronic unit 16 of FIG. 1, in particular by a microprocessor, such as described above. Boundary value problems are commonly known in various branches of mathematics and physics, in particular in electrostatics and elasticity. From a knowledge of physical parameters on a boundary, values within the boundary can be mathematically calculated. Thus a uniform variation in transmitivity over the lens in respond to the direction and intensity of the incident light can be calculated.

Figure 21:
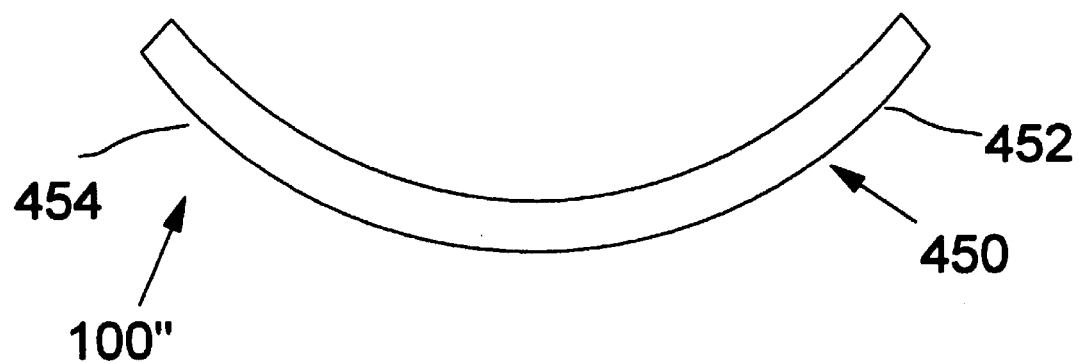
FIG. 21 is a view of the shutter 100" of FIG. 20 in the direction of arrow 440.

FIG. 21 is a view of the shutter 100" of FIG. 20 in the direction of arrow 440. In FIG. 21 the shutter is shown curved. The shutter can be a single planar shutter, be made up of a plurality of planar regions, be cured in an arbitrary shape and the like. The incident radiation is in the direction of the arrow 450. Thus side 452 of shutter 100" will be darker than side 454 of shutter 100". The transmitivity will continuously vary from side 452 to side 454.

Figure 22:
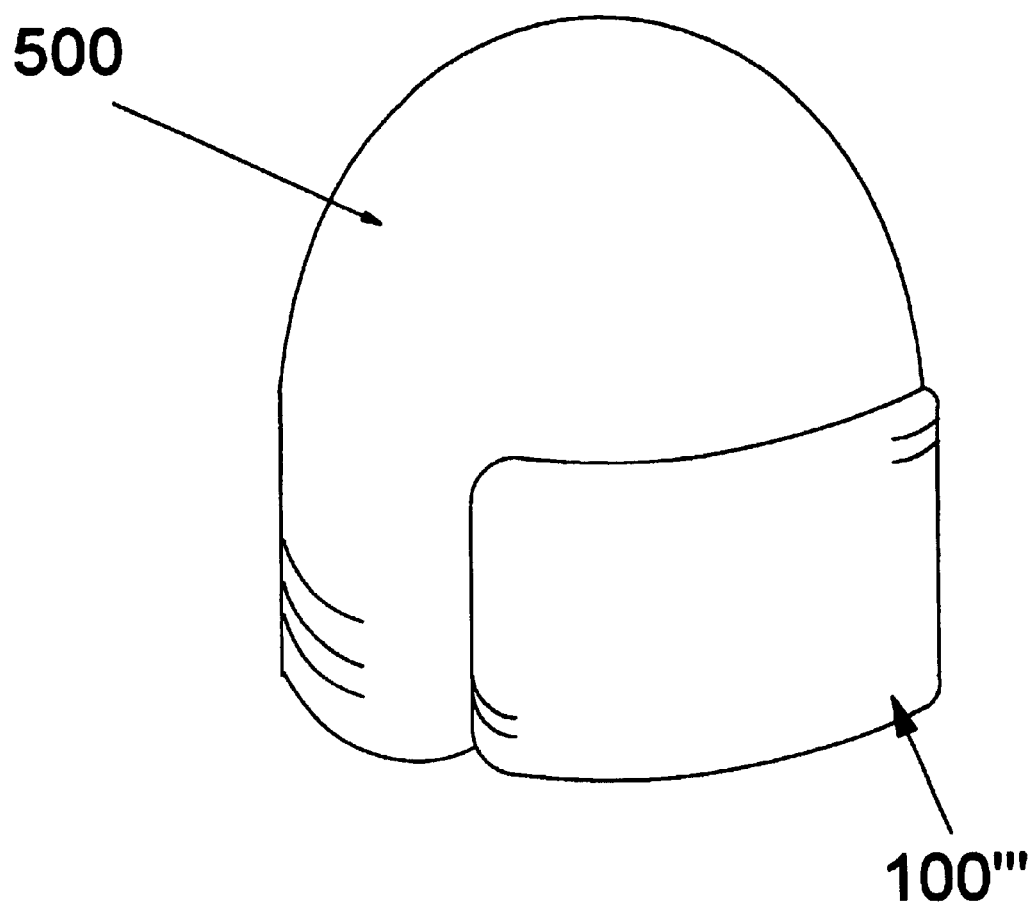
FIG. 22 is a schematic diagram of a helmet having a light shutter according to the present invention.

FIG. 22 is a schematic diagram of a helmet 500 having a light shutter 100". The helmet can be a skiing helmet, a racing car helmet or any other helmet. Rather than being a helmet, the radiation shutter 100" can be goggles with one or more lenses. Any one of the embodiments can be applied to the helmet or goggles. In the embodiment of FIG. 20 with a plurality of radiation sensitive regions is particularly advantageous for example in a skiing helmet or goggles. When a skier is skiing on a down hill slope, the skier's field of view changes rapidly. One moment the skier can be skiing into the sun, the next moment the skier can be skiing in a treed area where the sun is blocked from view and the next moment the skier can be skiing into an up hill slope with the sun at the skier's back so that there is a lot or sun glare off the snow. The eye shades according to the present invention can rapidly respond to the changing light conditions and adjust the transmitivity to the shade lens to the intensity and direction of the light. The user of the shades according to the present invention, in particular the embodiment with a plurality of light sensitive regions, sees a more uniform light intensity in the user's field of view than is seen using a conventional lens of goggles. In a conventional lens of goggles the light will me more intense in the direction of the sun or sun glare. The teaching of the present invention is applicable to a wide variety of situations. For example, a person on the interior of an automobile is in a similar situation to the user of a helmet, such as shown in FIG. 22. The front, back and side windows (all windows) can be shades or lenses of any type according to the present invention. The windows can independently change transmitivity, distribution of transmitivity and color automatically or manually adjusted as taught herein. A house having a plurality or windows is also similar to the situation of FIG. 22. Each window of a house can be a shutter or lens according to the teaching of the present invention. Each window can change its transmitivity in response to the incident light intensity automatically or manually by the user. Each window can have a uniform transmitivity or a non-uniform transmitivity. Each window can have the same or a different color which is automatically or manually determined. Each window of any embodiment herein can have a non-uniform color distribution separately or in combination with non-uniform transmitivity distribution.

An eye shade apparatus includes any apparatus to shade the view of a user and includes eye glasses, goggles, face masks, skiing masks and goggles, diving, helmets with face protection visors and masks, windows, such as automobile windows, house windows and the like. The term eye shade apparatus is generic. It means any apparatus which modifies the field of view when an eye looks through the apparatus at a scene in the field of view. The term light as used herein means any wave length of electromagnetic radiation. The teachings of U.S. Pat. Nos. 3,245,315; 5,113,270; 5,276,539; 4,241,286; 5,519,522; 5,208,688; and, 5,751,258 are incorporated herein by reference.

What is claimed is:

1. An eye shade apparatus comprising a variable transmission comprising:
    an electo-optic lens;
    a variable power source for controlling the transmission of said electro-optic lens to have a nonuniform light transmission; and
    said apparatus comprises four electro-optic lenses which comprises two side lenses and two forward lenses, and four photosensitive regions, one for each of said four electro-optic lenses.

2. An eye shade apparatus comprising a variable transmission comprising:
    an electo-optic lens;
    a variable power source for controlling the transmission of said electro-optic lens to have a nonuniform light transmission;
    said electro-optic lens comprises a plurality of regions, said variable power source comprises a plurality of power outputs, each of said plurality of power outputs corresponds to at least one of said plurality or regions;
    said variable power source comprises a photosensitive control to vary said power source in response to the intensity of light incident on said eye shade apparatus;
    a plurality of said photosensitive regions;
    said plurality of said photosensitive regions provide said nonuniform light transmission; and
    a programable processor to determine said nonuniform light transmission from responses of said photosensitive regions.

\* \* \* \* \*